United States Patent
Turdjian et al.

(10) Patent No.: US 8,413,663 B2
(45) Date of Patent: Apr. 9, 2013

(54) PUSH-IN TYPE OF EARPLUG WITH IMPROVED INSERTION STEM

(75) Inventors: Crest Turdjian, Los Angeles, CA (US); Mark Magidson, Los Angeles, CA (US)

(73) Assignee: Moldex Metric, Inc., Culver City, CA (US)

( * ) Notice: Subject to any disclaimer, the term of this patent is extended or adjusted under 35 U.S.C. 154(b) by 0 days.

(21) Appl. No.: 12/931,582

(22) Filed: Feb. 4, 2011

(65) Prior Publication Data

US 2012/0199143 A1    Aug. 9, 2012

(51) Int. Cl.
*A61F 11/00* (2006.01)
*A61B 7/02* (2006.01)

(52) U.S. Cl. ........................... 128/864; 181/135

(58) Field of Classification Search .............. 607/55–57; 181/126, 128, 130, 135, 129; 381/1, 23.1, 381/312, 313, 322, 328, 329, 150, 182, 370, 381/374, 380–382, 326, FOR. 133; 128/846, 128/857, 864–868; 623/10
See application file for complete search history.

(56) References Cited

U.S. PATENT DOCUMENTS

| | | | |
|---|---|---|---|
| 2,458,884 A | 1/1949 | Volkmann | |
| 3,440,314 A | 4/1969 | Frisch | |
| 5,201,007 A | 4/1993 | Ward et al. | |
| D369,655 S | 5/1996 | Esler et al. | |
| D375,550 S | 11/1996 | Esler et al. | |
| D375,551 S | 11/1996 | Esler et al. | |
| 5,682,020 A | 10/1997 | Oliveira | |
| 5,792,998 A | 8/1998 | Gardner, Jr. et al. | |
| 5,996,584 A | 12/1999 | Oliveira et al. | |
| 6,310,961 B1 | 10/2001 | Oliveira et al. | |
| 7,464,786 B2 * | 12/2008 | Falco et al. | 181/135 |
| 2007/0102006 A1 | 5/2007 | Falco | |

FOREIGN PATENT DOCUMENTS

WO    WO2012026864 A1    3/2012

* cited by examiner

*Primary Examiner* — Patrica Bianco
*Assistant Examiner* — Tarla Patel
(74) *Attorney, Agent, or Firm* — Charles H. Schwartz

(57) ABSTRACT

A hearing protective earplug for insertion into the human ear canal of a user where the human ear canal has sidewalls and a typical curved portion. A soft resilient body has a main body element with a front end for insertion in the human ear canal. An elongated stem has two ends with one end attached to the main body element. The stem extends outward from the main body element and away from the front end. The other end of the stem forms a handle portion of the stem. The stem is sufficiently stiff as to allow manipulation of the main body element into the ear canal of the user. The stem member has a crooked or wavy configuration within the ear canal as it extends outward from the main body to the handle portion of the stem. As the front end of the main body element is inserted into the ear canal, the stem member is rotated during insertion with the handle portion to fit around the typical curved portion in the human ear canal. This seats the main body to acoustically block the ear canal while at the same time spaces the stem member within the typical curved portion of the ear canal to minimize contact with the sidewalls of the ear canal.

24 Claims, 4 Drawing Sheets

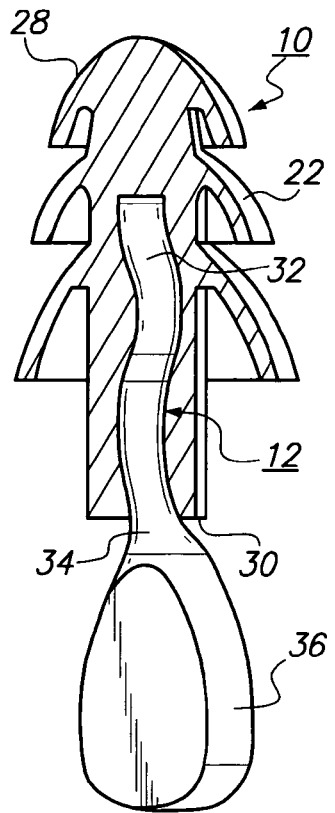
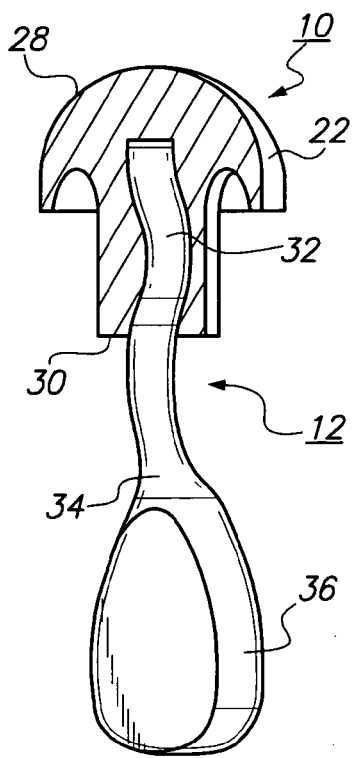
FIG. 4   FIG. 5
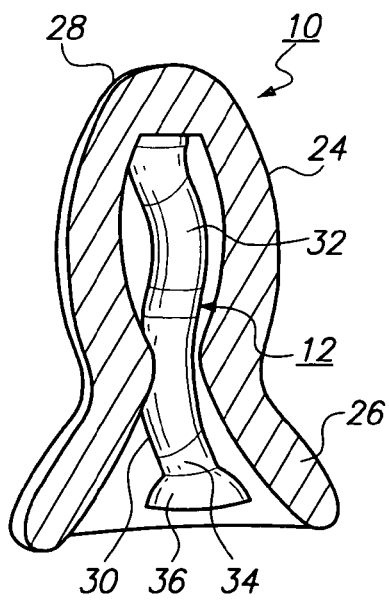
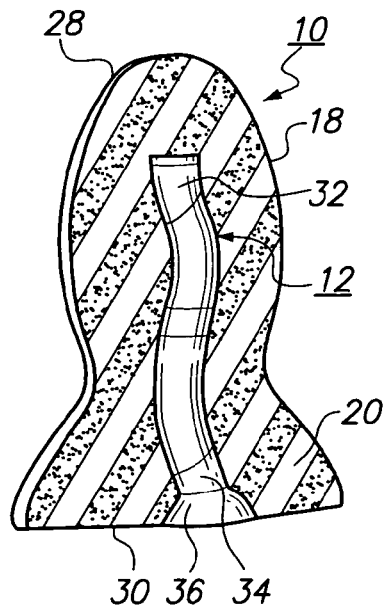
FIG. 6   FIG. 7

PUSH-IN TYPE OF EARPLUG WITH IMPROVED INSERTION STEM

BACKGROUND OF THE INVENTION

The present invention relates generally to hearing protective earplugs and is more particularly concerned with pre-molded earplugs of the push-in type. Specifically, the present invention relates to a new concept for an insertion stem for push-in type of earplugs that permits easy and deep insertion of the earplug with less pressure and less contact of the stem with the sidewalls of the ear canal. This earplug will fit and provide comfortable sound attenuation to a larger number of individuals than prior art earplugs.

Pre-molded earplugs are composed of different materials. One such material is resilient polymer foam material such as foam rubber, polyurethane or plasticized polyvinylchloride. For example, in U.S. Pat. No. 5,188,123 there is disclosed a push-in type earplug comprising a soft, elastic foam body element having a stiff axially oriented stem by which to facilitate insertion and removal of the body element into and from the ear canal. Another type of push-in earplug includes a central shaft and extending there from at a front end at least a single flange member. These earplugs are generally composed of an injection molded resilient elastomer material such as synthetic rubber material or natural rubber. The flange element extends rearward from the front end of the shaft member and also extends rearward from the front end and is so spaced so as to provide a free annular space between the flange and the shaft. An earplug of this type may be seen in U.S. Pat. No. 5,957,136.

A major problem generally incurred with all of these pre-molded earplugs of the prior art resides in the anatomical fact that the human ear canal is quite variable in size and geometry. Substantially, all ear canal include at least one curved section so that there is not a straight path between the outside of the ear and the inner ear. This is a protective measure in the human ear to prevent a direct path to the inner ear, which could be compromised by a finger or a stick or any other foreign object. As a result, a single type of a pre-molded prior art earplug has not been found capable of accommodating the broad range of human ear canals in both size and geometry. Quite often in inserting the pre-molded earplugs of the prior art, the stem member cannot be manipulated to insert the front end to the proper position to maximize attenuation without incurring discomfort by touching the sidewall of the ear canal thereby irritating the ear canal during use of the earplug.

The great majority of the existing push-in types of earplugs have straight stems generally made out of relatively stiff plastic materials (for instance the earplug described in U.S. Pat. No. 5,188,123). However, to provide proper insertion, the plastic stem of this type of earplug should be flexible/bendable as the human ear canal is not straight and varies among individuals in size and shape. However, to bend a plastic stem inside the ear canal may not be ideal and can increase the pressure and may not be comfortable for the wearer either during insertion or during wear.

In U.S. Pat. No. 3,811,437 and Reissue Pat.No. 29,487, roll down type hearing protective earplugs composed of viscoelastic polymeric foam are shown to be compressed, inserted into the ear canal and therein allowed to expand to result in a comfortable and complete acoustic blocking of the ear canal. This type of earplug does conform to the shape of the ear canal but with current types of stem-mounted earplugs, the stem portion does not. The roll down type of foam earplug possesses certain deficiencies that prevent their use in certain hearing protective situations. This type of earplugs is prepared for insertion by initially rolling it down between thumb and fingers to compress the earplug to below the size of the ear canal into which it is to be inserted. For hygiene reasons, the user's hands should be clean at the time of use. In many noisy industrial environments, abrasive materials or harsh chemicals are present and can become imbedded in the earplug. Since these contaminants may be present on the user's hands, the first step of cleansing the hands can be a bother before using the earplugs. The present invention is directed to a design that will overcome the above deficiencies since the earplug is inserted using a stem member with a handle portion located outside of the ear canal.

OBJECT OF THE INVENTION

It is an object of the invention to provide a new and novel hearing protective earplug construction.

It is still another object of the invention to provide a new and novel earplug construction that may be used with either an injection molded resilient thermoplastic elastomer material such as synthetic rubber material or a viscoelastic polymeric foam type of material.

It is another object of the invention to provide an earplug construction which may be produced in a single size, but which provides easy insertion, wearer comfort and good sound attenuation to substantially the entire adult population.

Other objects and advantages of the invention will in part be obvious and will in part appear hereinafter.

SUMMARY OF THE INVENTION

The earplug of the present invention includes a main body element having a front end. The main body element is of circular or ovoid cross section, and may be formed of either an injection molded resilient thermoplastic elastomer material, such as synthetic rubber material, or a viscoelastic polymeric foam type of material or other types of acoustic foam material that have a fast recovery. An elongated stem member is attached to the main body element and may be axially located in the main body and the stem member then extends outward and may terminate at an exterior position with a handle portion.

The stem member has a crooked or wavy configuration as it extends outward from the main body within the ear canal so that as the main body of the earplug is inserted into a user's ear canal, the stem member may be rotated during insertion with the handle portion to fit around the typical curved portion in the human ear canal to seat the main body to acoustically block the ear canal while at the same time spacing the stem member within the ear canal to minimize contact with the sidewalls of the ear canal. The crooked stem member may be either axially in line with the main body or may be axially offset or eccentric along its length to increase the spacing effect during the rotation of the earplug within the ear canal. The crooked stem member may include one or more portions that are angularly displaced from adjacent portions along the length of the stem member and with such angularly displaced adjacent stem portions being curved or straight within certain dimensional ranges to fit substantially the entire adult population.

In the present invention there is no need to bend the stem to insert the earplug. Just by twisting and/or pushing the handle portion of the stem member during the insertion, the user is able to find the best position for the stem to be spaced from the sidewalls in the typical curved portion of the human ear canal. The stem member within the ear canal has less contact with the walls of the ear canal (less pressure) because of the angularly displaced adjacent stem portions being curved or straight within certain dimensional ranges forming the crooked configuration. The curved or straight angularly displaced adjacent stem portions can be two or three dimensional in nature and are designed to provide a comfortable fit to a large number of the population. In addition, as indicated above, for more versatility the rear end of the stem member that carries the earplug body could be eccentric against the centerline of the main body of the earplug so as to enhance the rotational effect.

BRIEF DESCRIPTION OF THE DRAWING

FIG. 4 is a front perspective view, partly in section, of a variation of the embodiment of the earplug of FIG. 3 in accordance with the invention, FIG. 5 is a front perspective view, partly in section, of another embodiment of an earplug in accordance with the invention having a similar rounded nose member to the embodiment of FIG. 2, FIG. 6 is a front perspective view, partly in section, of another embodiment of an earplug in accordance with the invention and having a flange portion lying outside the ear, FIG. 7 is a front perspective view, partly in section, of still another embodiment of an earplug in accordance with the invention and having a flange portion lying outside the ear.

DESCRIPTION OF THE PREFERRED EMBODIMENTS

Figure 1:
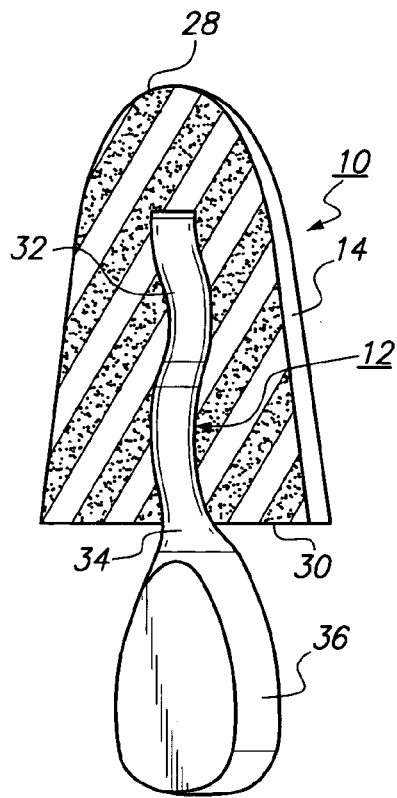
FIG. 1 is a front perspective view, partly in section, of an earplug in accordance with the invention.

Referring now to FIGS. 1 through 7, embodiments of the present invention are shown and the same reference numerals refer to the structures having a similar function including a main body element 10 and an elongated stem member 12 extending outward and axially from the and at least partially within the main body element or attached to the main body element 10.

Figure 2:
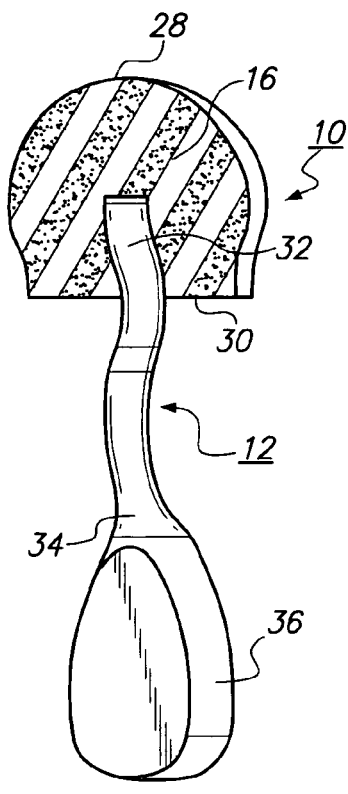
FIG. 2 is a front perspective view, partly in section, of another embodiment of an earplug in accordance with the invention.
Figure 3:
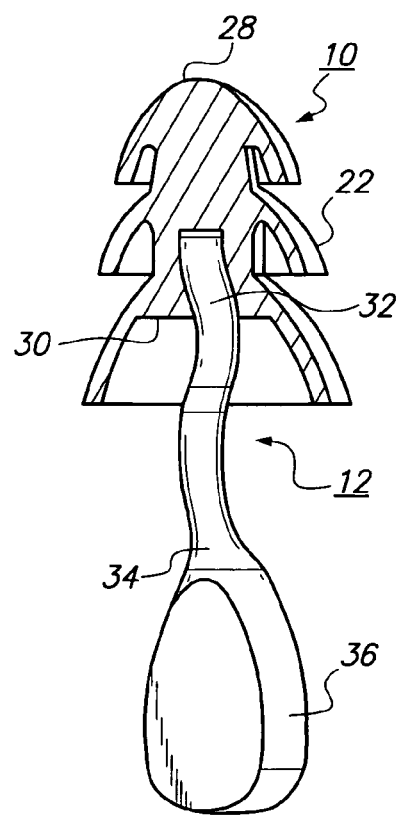
FIG. 3 is a front perspective view, partly in section, of still another embodiment of an earplug in accordance with the invention.

In FIGS. 1, 2 and 7, the earplug construction of the invention uses a soft, resilient polymeric foam body each comprising a smoothly contoured, homogenous, viscoelastic main body element adapted in size and shape to be inserted into the human ear canal. In FIG. 1, the main body element has a bullet shape 14 and in FIG. 2 the main body element has a hemispheric pod shape 16. In FIG. 7, the main body element has an elongated bulbous curved shape 18 including a flange portion 20. In FIGS. 3-6, the main body element 10 is an injection molded resilient elastomer material such as synthetic or natural rubber material and in FIGS. 3-5 has lateral projections in the nature of one or more flange elements 22. In FIG. 6, the main body element 10 has an elongated bulbous curved shape 24 with a flange portion 26. Each main body element 10 has a front end 28 and a base end 30. While the preferred cross sectional shape of the main body element 10 is circular, it will be appreciated that the cross sectional shape may also be ovoid or elliptical.

The stem member 12 is an elongated member that may be tubular or solid throughout its cross section and may be uniform or non-uniform along its length. In a preferred structure, the elongated stem has two ends, one end 32 is located in and, in some embodiments, secured to the interior of the front end portion 28 of the main body element 10. The stem 12 then extends axially and outward from the front-end portion 28 and through the base end 30. The other end 34 of the stem may terminate at a point exterior to or adjacent to the base end 30 and forms a handle portion 36 of the stem 12. The stem is sufficiently stiff so as to allow manipulation of the main body element 10 so that the earplug can be seated in the ear canal for maximum attenuation while at the same time being rotated to ensure clearance between the stem member and the sidewalls of the ear canal.

As can be seen in FIGS. 1-7, the stem 12 and, in particular, the portion of the stem between the one end 32 and the handle portion 36 has a crooked or wavy configuration and specifically has a curved or straight angularly displaced adjacent stem portions that would conform to the shape of a typical ear canal as it extends inward from the outside to the inner ear. Since there can be variations in the shape of the ear canal between different users of earplugs, the rotation of the earplug as it is being inserted into the ear canal creates the ability to accommodate these variations in the shape of the ear canal by changing the position of the curved or straight angularly displaced adjacent stem portions of the stem 12 in the ear canal.

The cross sectional dimension of the stem 12 should not be so great as to prevent easy insertion of the earplug into ear canals of small size. The stem 12 can be of any convenient length such that, for the embodiments of FIGS. 1-5, the handle portion 36 extends beyond the main body element 10. The handle portion may be formed as a flared end to provide an insertion and removal member for the main body element 10. The exact length selected for the stem 12 including the handle 36 will largely be a matter of choice but the dimensions of the portion of the stem between the one end 32 and the handle portion 36 will have a range in length and deviation from a center axis that will accommodate the largest number of variations in size and shape of ear canals. For the embodiments of FIGS. 6 and 7, the handle portion 36 is located adjacent the base end 30 of the main body element 10 but the same dimensional considerations for the stem 12 as to length and deviation from a center axis that will accommodate the largest number of variations in size and shape of ear canals will apply.

The crooked stem member may be either axially in line with the main body or may be axially offset or eccentric along its length to increase the spacing effect during the rotation of the earplug within the ear canal. The dimensions, geometry and material of construction employed for the stem 12 are selected so that the stem 12 is sufficiently stiff to allow manipulation of the main body element 10 so that the earplug can be seated in the ear canal for maximum attenuation while at the same time being rotated to ensure clearance between the stem member and the sidewalls of the ear canal.

The stem 12 may be constructed of any suitable material, paper, rubber, cardboard and plastic rod or tube may be used as long as the material is adequately stiff in nature and can be formed in the appropriate crooked or wavy configuration. It is important, for the embodiments of FIGS. 1-5, that the one end 32 of the stem 12 is attached to the main body element 10 with security as to avoid separation of the stem 12 from the main body element 10 during use. If separation occurs, it could be difficult to remove the earplug if it is inserted deeply into the ear canal and the stem is no longer available to assist in removal. This can be achieved in any known manner, such as the use of adhesives or by solvent or thermal welding or by the use of an attachment achieved by a mechanical lock. This attachment can occur with the stem member 12 partially inserted into the main body element 10 or the attachment can be provided right at the back end 30 of the main body element 10 by any of the means described above. Also, the main body element 10 may be affixed to the stem 12 thereof during the molding operation. The stem 12 can be utilized as an insert in the mold for the main body 10, the one end 32 acting as a male mold member for the main body element 10. As the molding formulation cures in the mold to form the main body element 10, the main body element 10 can bond firmly to the end 32 of the stem 12.

The embodiments of FIGS. 6 and 7 both include flared portions 26 and 20 for the embodiments of FIGS. 6 and 7, respectively. These flared portions 26 and 20 would normally prevent the earplug of these embodiments from entering the ear canal too deeply since the flared portions 26 and 20 restrict insertion once these flared portions abut the outside opening to the ear canal. However, even if the earplug is inserted deeper, still the flared portions 26 and 20 can be used to remove the earplug from the ear canal. Even if the stem 12 member, initially attached to the main body 10 by being located within the main body 10, becomes separated from the main body element 10, the flared portions 26 and 20 can be used to remove the earplug. In the embodiment of FIG. 7, the flared end 20 may completely enclose the handle portion of the stem member so that the stem member would not be visible but the stem and the main body member can still rotate to properly seat the earplug in the ear canal with the spacing of the stem member from the walls of the ear canal.

The contoured main body element 10 that extends from the front end 28 may be formed with a rounded configuration to aid insertion of the earplug. The length of the main body element 10 relative to its maximum cross sectional dimension is subject to considerable variation as can be seen in the various embodiments of the invention and is not normally critical. For example, the shape of main body element 10 of the earplug shown in FIGS. 2 and 5 each include a hemispheric pod portion and their length to diameter ratio contrasts with the embodiments of FIGS. 1, 6 and 7, where the body elements 10 are elongated and have a larger length to diameter ratio. Similarly, the embodiments of FIGS. 3 and 4 also are elongated and have a larger length to diameter ratio.

Figure 8:
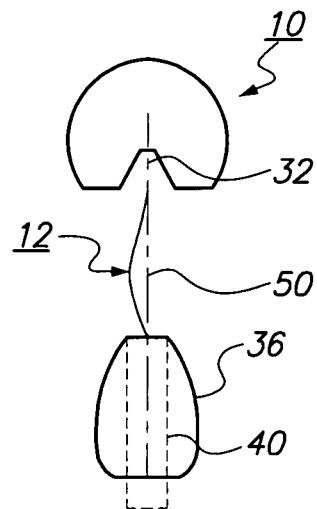
FIG. 8 is a schematic drawing representing any of the earplugs of FIGS. 1-7 and showing the stem member axially in line with the main body of the earplug with a stem member having a curved shape.
Figure 9:
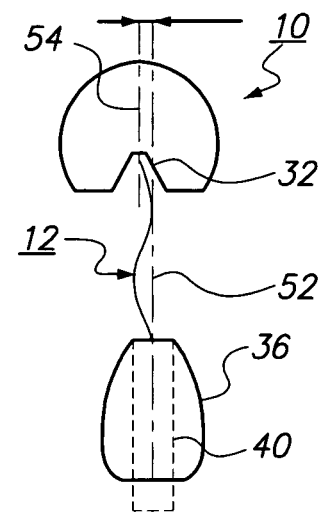
FIG. 9 is a schematic drawing representing any of the earplugs of FIGS. 1-7 and showing the stem member axially offset or eccentric along its length with the main body axis of the earplug with a stem member having a curved shape.
Figure 8A:
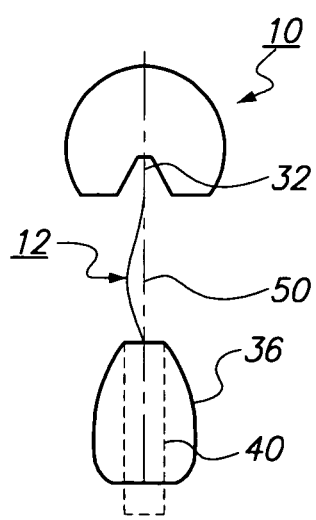
FIG. 8A is a schematic drawing representing any of the earplugs of FIGS. 1-7 and showing the stem member axially in line with the main body of the earplug with a stem member having straight angularly displaced adjacent stem portions.
Figure 9A:
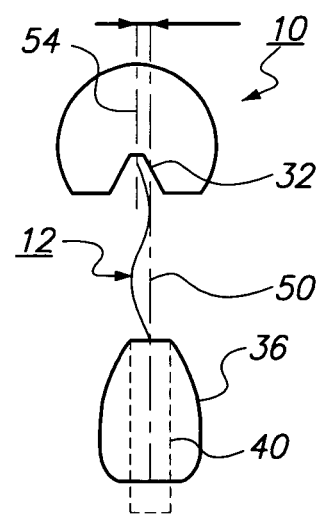
FIG. 9A is a schematic drawing representing any of the earplugs of FIGS. 1-7 and showing the stem member axially offset or eccentric along its length with the main body axis of the earplug with a stem member having straight angularly displaced adjacent stem portions.

FIGS. 8, 8A, 9 and 9A illustrate in schematic form generalized versions of the earplug of the present invention and showing in FIGS. 8 and 8A the stem member axially in line with the main body of the earplug and in FIGS. 9 and 9A the stem member axially offset or eccentric along its length with the main body of the earplug. Also, the range of dimensions for the crooked or wavy portion of the stem 12 are shown with preferred dimensions to provides easy insertion, wearer comfort and good sound attenuation to substantially the entire adult population. The main body element 10 shown in FIGS. 8, 8A, 9 and 9A represent any of the embodiments of FIGS. 1-7. Similarly, the handle portion 36 of the stem 12 may have the flattened configuration shown in FIGS. 1-5 or may have the design shown in FIGS. 6 and 7 or may even be nothing more than an extension 40 of the stem 12 as shown by dotted lines in FIGS. 8, 8A, 9 and 9A.

In FIGS. 8 and 9, the stem member is shown to have a curved shape and with the stem member of FIG. 8 having a simpler curved shape composed of curved stem portions compared to the curved shape of the stem member of FIG. 9. Similarly, in FIGS. 8A and 9A, the stem member has straight angularly displaced adjacent stem portions and with the stem member of FIG. 8A having two straight angularly displaced adjacent stem portions and the stem member of FIG. 9A having three straight angularly displaced adjacent stem portions. It will be appreciated that simpler shape stem member of FIGS. 8 and 8A may be used either with the axis inline, as shown in FIGS. 8 and 8A, or offset, as shown in FIGS. 9 and 9A, and the same for the more complex shape stem member of FIGS. 9 and 9A. Also, the stem member can also be formed by a combination of curved and straight angularly displaced adjacent stem portions. With both the curved shape stem member and straight angularly displaced adjacent stem portions or combination thereof, the number of stem portions may be varied as long as the stem member can accommodate a large variety of shapes of ear canals of the human population.

As shown in FIGS. 8, 8A, 9 and 9A, the distance between the one end 32 of the stem member 12 and any shape handle portion 36 of the stem member 12 should range between 6 mm to 25 mm with a preferred distance of 14 mm. In FIGS. 8 and 8A, the handle portion 36 and the main body element 10 are located along the same axis 50 and the range of maximum deviation from the axis 50 by the crooked or wavy portion of the stem member 12 being 0.8 mm to 6 mm and with a preferred maximum deviation being 1.3 mm. In FIGS. 9 and 9A the handle portion 36 is offset from the main body element 10 and the handle portion 36 and the main body element 10 are located along two parallel axes 52 and 54. The range of maximum deviation between the axis 52 and 54 by the crooked or wavy portion of the stem member 12 being 0.8 mm to 6 mm and with a preferred maximum deviation being 1.3 mm. The crooked stem member may be either axially in line with the main body as in FIGS. 8 and 8A or may be axially offset or eccentric along its length as in FIGS. 9 and 9A to increase the spacing effect during the rotation of the earplug within the ear canal.

Figure 10A:
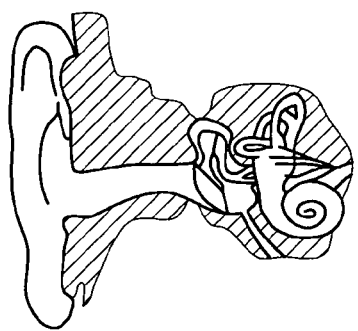
FIGS. 10A-E illustrate a typical ear canal and the positioning of a prior art earplug in FIG. 10B and FIG. 10C and earplugs of the present invention in FIGS. 10D and 10E.
Figure 10B:
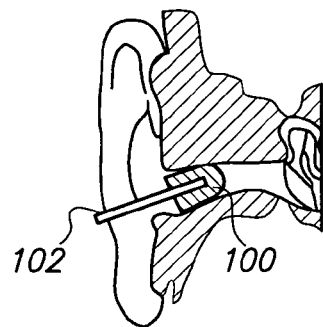
Figure 10C:
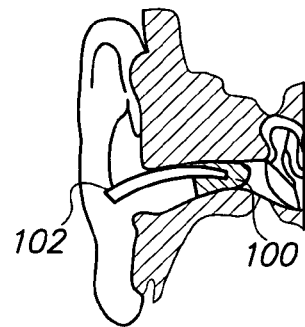
Figure 10D:
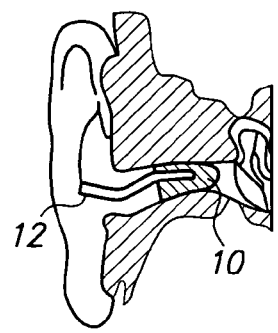
Figure 10E:
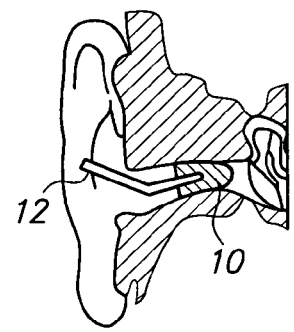

FIGS. 10A-E illustrate a typical ear structure and the positioning of a prior art earplug in the ear canal in FIGS. 10B and 10C and the positioning of the earplugs of the present invention in the ear canal FIGS. 10D and 10E. In FIG. 10A it can be seen that the typical ear structure includes the curved structure of the external auditory meatus or ear canal with sidewalls leading to the eardrum. In appearance, it is a slightly curved tube that extends inward from the floor of the auricle, or protruding portion of the outer ear, and ends blindly at the eardrum membrane, which separates it from the middle ear. FIGS. 10B and 10C illustrate a prior art earplug having a main body element 100 and a straight stem 102. FIG. 10B shows the earplug initially inserted to block the ear canal and as the earplug is more fully inserted to increase the attenuation of outside noise, as shown in FIG. 10C, the stem 102 will be bent as it touches the sidewalls and be uncomfortable to the user due to the contact of the stem with the sidewalls of the ear canal. FIGS. 10D and 10E show any of the embodiments of FIGS. 1-7 with the main body element 10 and stem member 12 fully inserted into the ear canal and with the stem member 12 positioned to be clear of the sidewalls of the ear canal to minimize contact with the sidewalls. FIG. 10D illustrates the stem member 12 to have a curved shape as shown in FIGS. 8 and 9 and FIG. 10E illustrates the stem member 12 to have straight angularly displaced adjacent stem portions as shown in FIGS. 8A and 9A.

Figure 11:
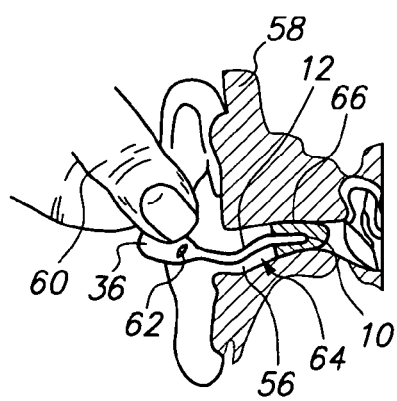
FIG. 11 is an illustration that represents any of the earplugs of FIGS. 1-5 being inserted into the ear canal and with the stem member being manipulated so that the earplug can be seated in the ear canal for maximum attenuation while at the same time being rotated to ensure clearance between the stem member and the sidewalls of the ear canal.

FIG. 11 illustrates the main body element 10 of the earplug and in particular represents the embodiments of FIGS. 1-5 being inserted into an ear canal 56 of a human subject 58 and with the stem member 12 being manipulated by the fingers 60 of the human subject 58 so that the earplug can be seated in the ear canal 56 for maximum attenuation while at the same time being rotated as shown by arrow 62 to ensure clearance to minimize contact between the stem member 12 and sidewalls 64 of the typical curved portion 66 in the human ear canal 56. If the crooked stem member 12 is axially offset or eccentric along its length as in FIG. 5, this increases the spacing effect during the rotation of the stem member within the ear canal.

Figure 12:
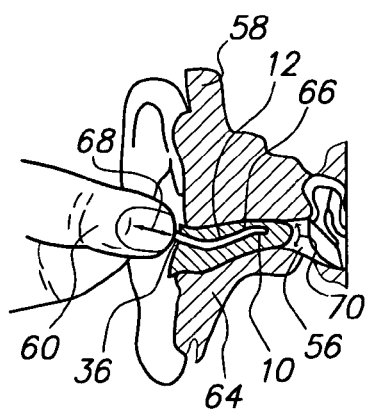
FIG. 12 is an illustration that represents either of the earplugs of FIGS. 6 and 7 being inserted into the ear canal and with the stem member being manipulated by being pushed in so that the earplug can be seated in the ear canal for maximum attenuation while at the same time the stem member rotated to ensure clearance between the stem member and the sidewalls of the ear canal.

FIG. 12 illustrates the main body element 10 of the earplug and in particular represents the embodiments of FIGS. 6 and 7 being inserted into an ear canal 56 of a human subject 58 and with the handle portion 36 and thereby the stem member 12 being pushed in as shown by arrow 68 by the fingers 60 of the human subject 58 so that the earplug can be seated to fit around the typical curved portion in the human ear canal 56 for maximum attenuation while at the same time the stem member 12 rotates as shown by arrow 70 to ensure clearance between the stem member 12 and sidewalls 64 of the ear canal 56. The rotation of the stem member 12 occurs during insertion since the stem member adjusts to the shape of the ear canal to find the path of least resistance. If the crooked stem member is axially offset or eccentric along its length as in FIGS. 9 and 9A, this increases the spacing effect during the rotation of the stem member within the ear canal.

The present invention is not to be limited to any specific design for the main body element or stem member including the handle portion of the stem member. There are a large number of designs currently used for a main body element of an earplug and the only limiting requirement for the present invention is that the main body element be capable of being inserted a significant distance into the ear canal to provide high attenuation levels. Similarly, the handle portion of the stem member can take any form as long as it can be manipulated by a user of the earplug. Therefore, the handle portion can be flat, round, oval, straight or bent or any other shape and can be merely an extension of the stem itself.

Several human subjects, having varying ear canal sizes and geometries, have used the earplugs of the present invention in noisy environments. These subjects have reported that the earplugs were easy to use, were comfortable throughout insertion, wearing and removal and provided adequate attenuation for their needs.

Although the invention has been described and shown with using specific preferred embodiments, it is to be appreciated that various adaptations and modifications may be made and the invention is only to be limited by the appended claims.

We claim:

1. A hearing protective earplug insertable into a human ear canal having sidewalls and a typical curved portion, comprising,
 a soft main resilient body having a main body element having a front end and an exterior shape,
 an elongated stem having two ends, one end attached to the main body element, the stem extending outward from the main body element and away from the front end, the other end of the stem forming a handle portion of the stem, the stem being sufficiently stiff as to allow manipulation of the main body element during insertion into the ear canal
 the stem member having a portion with a crooked or wavy configuration as it extends outward from the main body to the handle portion of the stem and so that during insertion of the front end of the main body element into the ear canal, rotation of the stem member with the handle portion will fit the stem member around the typical curved portion in the human ear canal so as to seat the main body element to acoustically block the ear canal while at the same time spacing the stem member within the typical curved portion of the ear canal to minimize contact with the sidewalls of the ear canal, and wherein the length of the crooked or wavy portion of the stem member as it extends outward from the main body to the handle portion has a range of 6 m to 25 m and wherein the stem member along the length of the crooked or wavy portion having at least three changes in direction along the length.

2. The earplug of claim 1 wherein the exterior shape of the main body element is bullet shaped.

3. The earplug of claim 1 wherein the exterior shape of the main body element is a hemispherical pod shape.

4. The earplug of claim 1 wherein the exterior shape of the main body element has lateral projections in the nature of one or more flange elements.

5. The earplug of claim 1 wherein the exterior shape of the main body element is elongated to enclose a substantial portion of the length of the stem member.

6. The earplug of claim 1 wherein the exterior shape of the main body element is elongated to enclose substantially all of the length of the stem member.

7. The earplug of claim 1 wherein the exterior shape of the main body element is elongated to enclose substantially all of the length of the stem member and wherein the main body element includes a flared shape adjacent the handle portion of the stem member.

8. The earplug of claim 1 wherein the main body element is formed of a resilient foam material.

9. The earplug of claim 1 wherein the main body element is an injection molded resilient thermoplastic elastomer material such as synthetic rubber material.

10. The earplug of claim 1 length of the crooked or wavy portion has a preferred length of 14 mm.

11. The earplug of claim 1 wherein the handle portion of the stem and the main body element are located along the same axis.

12. The earplug of claim 1 wherein the handle portion of the stem and the main body element are located along the same axis and wherein the crooked or wavy portion of the stem provides a deviation from the same axis and with the maximum deviation from the axis by the crooked or wavy portion of the stem is in a range between 0.8 mm to 6 mm.

13. The earplug of claim 1 wherein the handle portion of the stem and the main body element are located along the same axis and the preferred maximum deviation from the axis by the crooked or wavy portion of the stem is 1.3 mm.

14. The earplug of claim 1 wherein the handle portion of the stem is offset from the main body element and the handle portion of the stem and the main body element are located along two separate axes and wherein the crooked or wavy portion of the stem provides a deviation from the two separate axes and with the maximum deviation between the axes by the crooked or wavy portion of the stem is in a range between 0.8 mm to 6 mm.

15. The earplug of claim 1 wherein the handle portion of the stem is offset from the main body element and the handle portion of the stem and the main body element are located along two separate axes and the preferred maximum deviation between the axes being 1.3 mm.

16. The earplug of claim 1 wherein the stem member having the crooked or wavy configuration as it extends outward from the main body and within the ear canal is formed into a curved shape and wherein the rotation of the stem as it is being inserted into the ear canal accommodates variations in the shape of the ear canal by changing the position of the curved shape portion of the stem in the ear canal.

17. The earplug of claim 1 wherein the stem member having the crooked or wavy configuration as it extends outward from the main body and within the ear canal is formed into a curved shape and wherein the handle portion of the stem and the main body element are located along the same axis and wherein the curved shape provides a deviation from the same axis with the maximum deviation from the axis by the portion of the stem formed into a curved shape is in a range between 0.8 mm to 6 mm.

18. The earplug of claim 1 wherein the stem member having the crooked or wavy configuration as it extends outward from the main body and within the ear canal is formed into a curved shape and wherein the handle portion of the stem is offset from the main body element and the handle portion of the stem and the main body element are located along two separate axes and wherein the curved shape provides a deviation from the two separate axes and with the maximum deviation between the axes by the portion of the stem formed into a curved shape is in a range between 0.8 mm to 6 mm.

19. The earplug of claim 1 wherein the stem member having the crooked or wavy configuration as it extends outward from the main body and within the ear canal is formed with straight angularly displaced adjacent stem portions and wherein the rotation of the stem as it is being inserted into the ear canal accommodates variations in the shape of the ear canal by changing the position of the straight angularly displaced adjacent stem portions of the stem in the ear canal.

20. The earplug of claim 1 wherein the stem member having the crooked or wavy configuration as it extends outward from the main body and within the ear canal is formed with straight angularly displaced adjacent stem portions and wherein the handle portion of the stem and the main body element are located along the same axis and the range of maximum deviation from the axis by the portion of the stem formed with straight angularly displaced adjacent stem portions is between 0.8 mm to 6 mm.

21. The earplug of claim 1 wherein the stem member having the crooked or wavy configuration as it extends outward from the main body and within the ear canal is formed with straight angularly displaced adjacent stem portions and wherein the distance between the one end of the stem and the handle portion of the stem has a range between 6 mm to 25 mm and wherein the handle portion of the stem is offset from the main body element and the handle portion of the stem and the main body element are located along two separate axes and the range of maximum deviation between the axes by the portion of the stem formed with straight angularly displaced adjacent stem portions is between 0.8 mm to 6 mm.

22. The earplug of claim 1 wherein the handle portion of the stem is formed as a flattened portion of the stem.

23. The earplug of claim 1 wherein the handle portion of the stem is formed as an enlarged portion of the stem.

24. The earplug of claim 1 wherein the handle portion of the stem is formed as a continuation of the stem.

* * * * *